(12) United States Patent
Curtis

(10) Patent No.: US 9,017,958 B2
(45) Date of Patent: Apr. 28, 2015

(54) METHOD OF SIMULTANEOUS DETECTION OF HEPARIN-INDUCED IMMUNOGLOBULINS TYPES G, A, AND M

(71) Applicant: Blood Center Research Foundation, Milwaukee, WI (US)

(72) Inventor: Brian R. Curtis, Milwaukee, WI (US)

(73) Assignee: BloodCenter Research Foundation, Inc., Milwaukee, WI (US)

( * ) Notice: Subject to any disclaimer, the term of this patent is extended or adjusted under 35 U.S.C. 154(b) by 0 days.

(21) Appl. No.: 14/193,391

(22) Filed: Feb. 28, 2014

(65) Prior Publication Data
US 2014/0315223 A1    Oct. 23, 2014

Related U.S. Application Data

(60) Provisional application No. 61/776,959, filed on Mar. 12, 2013.

(51) Int. Cl.
G01N 33/00    (2006.01)
G01N 33/68    (2006.01)
G01N 33/86    (2006.01)

(52) U.S. Cl.
CPC ............ *G01N 33/6854* (2013.01); *G01N 33/86* (2013.01); *G01N 2333/745* (2013.01)

(58) Field of Classification Search
None
See application file for complete search history.

(56) References Cited

U.S. PATENT DOCUMENTS

| 5,972,717 A * | 10/1999 | Aster et al. ................ 436/503 |
| 5,972,718 A * | 10/1999 | Moghaddam et al. ........ 436/506 |
| 2006/0024744 A1 * | 2/2006 | Mills et al. .................... 435/7.1 |

OTHER PUBLICATIONS

Gobbi et al., New Laboratory Test in Flow Cytometry for the Combined Analysis of Serologic and Ceullular Parameters in the Diagnosis of Heparin-Induced Thrombocytopenia, Cytometry Part B (Clinical Cytometry) 58B, 2004, pp. 32-38.*
Albrecht, L. and Winteroll, S.; Laboratory Diagnosis of HeparinInduced Thrombocytopenia and Monitoriing of Alternative Anticoagulants; Clin. Diagn. Lab. Immunol. Sep. 2003 vol. 10; 5 731-740; doi:10.1128/CDLI.10.5.731-740.2003.
Amiral, J., Wolf, M., et al.; Pathogenicity of IgA and/or IgM antibodies to heparin-PF4 Complexes in Patients with Heparin-induced Thrombocytopenia. Br.. Haematol. 1996; vol. 92(4): 954-959.
Arepally, G.M., Ortel, T.L., Heparin-induced thrombocytopenia. Annu. Rev. Med. 2010; vol. 61: 77-90.
Cuker, A., Cines, D.B.; How I Treat Heparin-induced Thrombocytopenia. Blood 2012; vol. 119: 2209-2218.
Davoren, A., Aster, R.H.; Heparin-induced thrombocytopenia and thrombosis. Am J Hematol. 2006; vol. 81 (1):36-44.
Go, A.S., Mozaffarian, D., Roger, V.L., et al.; Heart disease and stroke statistics—2013 update: a report from the American Heart Association. Circulation. 2013; vol. 127: e6-e245.
Gobbi, G., Mirandola, P., Tazzari, P.L., et al.; Flow Cytometry Detection of Serotonin Content and Release in Resting and Activated Platelets. Br. J. Haematol. Jun. 2003; vol. 121(6): 892-896.
Greinacher, A., Juhl, D., Strobel, U., et al.; Heparin-induced thrombocytopenia: A prospective study on the incidence, platelet-activating capacity and clinical significance of antiplatelet factor 4/heparin antibodies of the IgG, IgM, and IgA classes. J Thromb Haemost. 2007; vol. 5(8):1666-1673.
Hoffman, J., Larme, O., Scholander, E.; A new method for covalent coupling of heparin and other glycosaminoglycans to substances containing primary amino groups. Carbohydr Res vol. 117:328, 1983.
Lindhoff-Last, E., Gerdsen, F., Ackermann, H., Bauersachs, R.; Determination of heparin—platelet factor 4—IgG antibodies improves diagnosis of heparin-induced thrombocytopenia. Br J Haematol 2001; vol. 113: 886-890.
McFarland, J., Lochowicz, A., Aster R., et al.; Improving the Specificity of the PF4 ELISA in Diagnosing Heparin-induced Thrombocytopenia. Am J. Hematol. 2012; vol. 87: 776-81.
Rauova, L., Zhai, L., Kowalska, M.A., Arepally, G.M., et al.; Role of platelet surface PF4 antigenic complexes in heparin-induced thrombocytopenia pathogenesis: diagnostic and therapeutic implications. Blood. 2006, Mar. 15; vol. 107(6):2346-53.
Suh, J.S., Malik, M.I., Aster, R.H., Visentin, G.P.; Characterization of the humoral immune response in heparin-induced thrombocytopenia. Am J Hematol. 1997; vol. 54(3):196-201.
Suh, J.S., Aster, R.H., and Visentin, G.P.; Antibodies from patients with heparin-induced thrombocytopenia recognize multiple epitopes on heparin: PF4 complexes. Blood vol. 91:916-922, 1998.
Sullivan, M.J., Grady, S., McFarland, J., Curtis, B.R.; A Multiplex Flow Cytometry Bead Assay for Simultaneous Detection of IgG, IgA, IgM Heparin-Dependent Antibodies; Blood 2013; 122 (21).
Tazzari, P.L., Ricci, F., Vitale, M., et al.; Heparin-induced Thrombocytopenia: Detection of Antiheparin/PF4 Antibodies by Means of Heparin/PF4-coated Beads and Flow Cytometry. Transfus Med. Jun. 2002; vol. 12(3): 193-8.
Tomer, A., Massalunga, C., Abshire, T.C.; Determination of Heparin-induced Thrombocytopenia: A Rapid Flow Cytometric Assay for Direct Demonstration of Antibody-mediated Platelet Activation. Am. J. Hematology May 1999; vol. 61(1): 53-61.
(Continued)

*Primary Examiner* — Gary W Counts
(74) *Attorney, Agent, or Firm* — Quarles & Brady LLP

(57) ABSTRACT

The invention provides a method for detecting heparin-induced antibodies comprising a) binding a PF4-heparin antigen to a solid surface; b) incubating the bound PF4-heparin with a sample comprising heparin-induced antibodies to be detected; c) contacting the sample with at least two labeled secondary antibodies, wherein the secondary antibodies bind to heparin-induced antibodies present in the sample; d) detecting the presence of the labeled secondary antibodies using flow cytometry or a suitable method, wherein the heparin-induced antibodies bound to the secondary antibodies are identified. In one embodiment, the at least two secondary antibodies are anti-human antibodies which specifically bind to heparin-induced antibodies and are selected from the group consisting of Ig, IgG, IgA, and IgM.

5 Claims, 17 Drawing Sheets
(12 of 17 Drawing Sheet(s) Filed in Color)

(56) References Cited

OTHER PUBLICATIONS

US Cancer Statistics Working Group; United States Cancer Statistics: 1999-2009 Incidence and Mortality Web-based Report. Atlanta(GA): Department of Health and Human Services, Centers for Disease Control and Prevention, and National Cancer Institute; 2013. Available at http://apps.nccd.cdc.gov/uscs/toptencancers.aspx.

Warkentin, T.E.; Heparin-induced thrombocytopenia: pathogenesis and management. Br J Haematol 2003; vol. 121:535-555.

Warner, M.N., Pavord, S., Moore, J.C., et al.; Serum-induced platelet procoagulant activity: an assay for the characterization of prothrombotic disorders. J.Lab Clin Med. Feb. 1999; vol. 133(2): 129-33.

Whitlach, N.L., Kong, D.F., Metjian, A.D., Arepally, G.M., Ortel, T.L.; Validation of the high-dose heparin confirmatory step for the diagnosis of heparin-induced thrombocytopenia. Blood. Sep. 9, 2010; vol. 116(10):1761-6.

\* cited by examiner

| Probe | Ex (nm) | Em (nm) | MW | Notes |
|---|---|---|---|---|
| Reactive and conjugated probes | | | | |
| Hydroxycoumarin | 325 | 386 | 331 | Succinimidyl ester |
| Aminocoumarin | 350 | 445 | 330 | Succinimidyl ester |
| Methoxycoumarin | 360 | 410 | 317 | Succinimidyl ester |
| Cascade Blue | (375);401 | 423 | 596 | Hydrazide |
| Pacific Blue | 403 | | 406 | Maleimide |
| Pacific Orange | 403 | 551 | | |
| Lucifer yellow | 425 | 528 | | |
| NBD | | 539 | 294 | NBD-X |
| R-Phycoerythrin (PE) | 480;565 | 578 | 240 k | |
| PE-Cy5 conjugates | 480,565,650 | | | aka Cychrome, R670, Tri-Color, Quantum Red |
| PE-Cy7 conjugates | 480,565,743 | | | |
| Red 613 | 480,565 | 613 | | PE-Texas Red |
| PerCP | 490 | | | Peridinin chlorphyll protein |
| TruRed | 490,675 | | | PerCP-Cy5.5 conjugate |
| FluorX | 494 | 520 | 587 | GE Healthcare |
| Fluorescein | 495 | 519 | 389 | FITC; pH sensitive |
| BODIPY-FL | 503 | | | |
| TRITC | 547 | 572 | 444 | TRITC |
| X-Rhodamine | 570 | 576 | 548 | XRITC |
| Lissamine Rhodamine B | 570 | 590 | | |
| Texas Red | 589 | 615 | 625 | Sulfonyl chloride |
| Allophycocyanin (APC) | | | 104 k | |
| APC-Cy7 conjugates | | | | PharRed |
| Alexa Fluor dyes [antibody conjugates] (Molecular Probes) | | | | |
| Alexa Fluor 350 | 343 | 442 | 410 | |
| Alexa Fluor 405 | 401 | 421 | 1028 | |
| Alexa Fluor 430 | 434 | 540 | 702 | |

Figure 1 - A

| | | | | |
|---|---|---|---|---|
| Alexa Fluor 488 | 499 | 519 | 643 | QY 0.92 |
| Alexa Fluor 500 | 503 | 525 | 700 | |
| Alexa Fluor 514 | 517 | 542 | 714 | |
| Alexa Fluor 532 | 530 | 555 | 724 | QY 0.61 |
| Alexa Fluor 546 | 561 | 572 | 1079 | QY 0.79 |
| Alexa Fluor 555 | 553 | 568 | 1250 | QY 0.1 |
| Alexa Fluor 568 | 579 | 603 | 792 | QY 0.69 |
| Alexa Fluor 594 | 591 | 618 | 820 | QY 0.66 |
| Alexa Fluor 610 | 610 | 629 | 1285 | |
| Alexa Fluor 633 | 632 | 665 | 1200 | |
| Alexa Fluor 647 | 650 | 665 | 1300 | QY 0.33 |
| Alexa Fluor 660 | 663 | 691 | 1100 | |
| Alexa Fluor 680 | 680 | 702 | 1150 | |
| Alexa Fluor 700 | 696 | 719 | 1400 | |
| Alexa Fluor 750 | 752 | 776 | 1300 | |
| Alexa Fluor 790 | 782 | 804 | 1750 | |
| Cy Dyes | | | | |
| Cy2 | 489 | 506 | 714 | QY 0.12 |
| Cy3 | (512) 550 | 570 (615) | 767 | QY 0.15 |
| Cy3B | 558 | 572 (620) | 658 | QY 0.67 |
| Cy3.5 | 581 | 594 (640) | 1102 | QY 0.15 |
| Cy5 | (625) 650 | 670 | 792 | QY 0.28 |
| Cy5.5 | 675 | 694 | 1128 | QY 0.23 |
| Cy7 | 743 | 767 | 818 | QY 0.28 |
| DyLight dye (Pierce) | | | | |
| DyLight 350 | 353 | 432 | | |
| DyLight 405 | 400 | 420 | | |
| DyLight 488 | 493 | 518 | | |
| DyLight 549 | 562 | 576 | | |
| DyLight 594 | 593 | 618 | | |
| DyLight 633 | 638 | 658 | | |

Figure 1 - B

| | | | |
|---|---|---|---|
| DyLight 649 | | | |
| DyLight 680 | | | |
| DyLight 750 | | | |
| DyLight 800 | | | |
| Nucleic acid probes | | | |
| Hoechst 33342 | 343 | 483 | 616 | AT-selective |
| DAPI | 345 | | | AT-selective |
| Hoechst 33258 | 345 | 478 | 624 | AT-selective |
| SYTOX Blue | 431 | 480 | ~400 | DNA |
| Chromomycin A3 | 445 | 575 | | CG-selective |
| Mithramycin | 445 | 575 | | |
| YOYO-1 | 491 | 509 | 1271 | |
| Ethidium Bromide | 493 | 620 | 394 | |
| Acridine Orange | 503 | 530/640 | | DNA/RNA |
| SYTOX Green | 504 | 523 | ~600 | DNA |
| TOTO-1, TO-PRO-1 | 509 | 533 | | Vital stain, TOTO: Cyanine Dimer TO-PRO: Cyanine Monomer |
| Thiazole Orange | 510 | 530 | | |
| Propidium Iodide (PI) | 536 | 617 | 668.4 | |
| LDS 751 | 543;590 | 712;607 | 472 | DNA (543ex/712em), RNA (590ex/607em) |
| 7-AAD | 546 | | | 7-aminoactinomycin D, CG-selective |
| SYTOX Orange | 547 | 570 | ~500 | DNA |
| TOTO-3, TO-PRO-3 | | | | |
| DRAQ5 | | | 413 | (Biostatus) (usable excitation down to 488) |
| Cell function probes | | | | |
| Indo-1 | 361/330 | 490/405 | 1010 | AM ester. Low/High Ca++, |
| Fluo-3 | 506 | 526 | 855 | AM ester. pH > 6 |
| DCFH | 505 | 535 | 529 | 2'7'Dichorodihydrofluorescein, oxidized form |
| DHR | 505 | 534 | 346 | Dihydrorhodamine 123, oxidized form, light catalyzes oxidation |

Figure 1 - C

| SNARF | 548/579 | 587/635 | | pH 6/9 | | | | |
|---|---|---|---|---|---|---|---|---|
| Fluorescent Proteins | | | | | | | | |
| | | | | QY | BR | PS | Source | |
| Y66H | 360 | 442 | | | | | | |
| Y66F | 360 | | | | | | | |
| EBFP | 380 | 440 | | 0.18 | 9 | | Addgene | monomer |
| EBFP2 | 383 | 448 | | 0.56 | 18 | | Addgene | monomer |
| Azurite | 383 | 447 | | 0.55 | 14 | | | monomer |
| GFPuv | 385 | | | | | | | |
| T-Sapphire | 399 | | | 0.60 | 26 | 25 | | weak dimer |
| TagBFP | 402 | | 26k | 0.63 | 33 | ++ | Evrogen | monomer |
| Cerulean | 433 | | | 0.62 | 27 | 36 | | weak dimer |
| mCFP | 433 | | | 0.40 | 13 | 64 | | monomer |
| ECFP | 434 | | | 0.15 | 3 | | | |
| CyPet | 435 | | | 0.51 | 18 | 59 | | weak dimer |
| Y66W | 436 | | | | | | | |
| dKeima-Red | 440 | 616 | | 0.31 | 8 | | MBL | dimer |
| mKeima-Red | 440 | 620 | | 0.24 | 3 | | MBL | monomer |
| TagCFP | | 480 | | 0.57 | 29 | | Evrogen | dimer |
| AmCyan1 | | 489 | | 0.75 | 29 | | Clontech | tetramer |
| mTFP1 (Teal) | | 492 | | 0.85 | 54 | | | dimer |
| S65A | | | | | | | | |
| Midoriishi-Cyan | | | | 0.9 | 25 | | MBL | dimer |
| Wild Type GFP | | 508 | 26k | 0.7 | 16 | | | |

Figure 1 - D

| | | | | 7 | | | |
|---|---|---|---|---|---|---|---|
| S65C | 479 | 507 | | | | | |
| TurboGFP | 482 | 502 | 26 k | 0.53 | 37 | | Evrogen | dimer |
| TagGFP | 482 | 505 | 27k | 0.59 | 34 | ++ | Evrogen | monomer |
| TagGFP2 | 483 | 506 | 27k | 0.6 | 34 | ++ | Evrogen | monomer |
| AcGFP1 | 484 | 510 | 27k | 0.82 | 27 | | Clontech | |
| S65L | 484 | 510 | | | | | | |
| Emerald | 487 | 509 | | 0.68 | 39 | 0.69 | Invitrogen | weak dimer |
| S65T | 488 | 511 | | | | | | |
| EGFP | 488 | 507 | 26k | 0.60 | 34 | 174 | Addgene | weak dimer |
| Azami-Green | 492 | 505 | | 0.74 | 41 | | MBL | tetramer (monomeric available) |
| ZsGreen1 | 493 | 505 | 105k | 0.91 | 40 | | Clontech | tetramer |
| Dronpa-Green | 503 | 518 | | 0.85 | 81 | | MBL | photoswitchable |
| TagYFP | 508 | 524 | 27k | 0.62 | 47 | | Evrogen | monomer |
| EYFP | 514 | 527 | 26k | 0.61 | 51 | 60 | | weak dimer |
| Topaz | 514 | 527 | | 0.60 | 57 | | | monomer |
| Venus | 515 | 528 | | 0.57 | 53 | 15 | | weak dimer |
| mCitrine | 516 | 529 | | 0.76 | 59 | 49 | | monomer |
| YPet | 517 | 530 | | 0.77 | 80 | 49 | | weak dimer |
| TurboYFP | 525 | 538 | 26 k | 0.53 | 56 | | Evrogen | dimer |
| PhiYFP | 525 | 537 | 26.8 k | 0.40 | 52 | ++ | Evrogen | weak dimer |
| PhiYFP-m | 525 | 537 | 26.8 k | 0.3 | 48 | ++ | Evrogen | monomer |

Figure 1 - E

| | | | | 9 | | | |
|---|---|---|---|---|---|---|---|
| ZsYellow1 | 529 | 539 | | 0.65 | 13 | Clontech | tetramer |
| mBanana | 540 | 553 | | 0.70 | 4 | Clontech | monomer |
| Kusabira-Orange | 548 | 559 | | 0.60 | 31 | MBL | monomer |
| mOrange | 548 | 562 | | 0.69 | 49 | 9 | | monomer |
| mOrange2 | 549 | 565 | | 0.60 | 35 | Clontech | monomer |
| mKO | 548 | 559 | | 0.60 | 31 | 122 | | monomer |
| TurboRFP | 553 | 574 | 26 k | 0.67 | 62 | Evrogen | dimer |
| tdTomato | 554 | 581 | | 0.69 | 95 | 98 | Clontech | tandem dimer |
| DsRed-Express2 | 554 | 591 | | 0.42 | 15 | Clontech | |
| TagRFP | 555 | 584 | 27k | 0.48 | 48 | Evrogen | monomer |
| DsRed monomer | 557 | 592 | ~28k | 0.1 | 3.5 | 16 | Clontech | monomer |
| DsRed2 ("RFP") | 563 | 582 | ~110 k | 0.55 | 24 | Clontech | |
| mStrawberry | 574 | 596 | | 0.29 | 26 | 15 | Clontech | monomer |
| TurboFP602 | 574 | 602 | 26 k | 0.35 | 26 | Evrogen | dimer |
| AsRed2 | 576 | 592 | ~110 k | 0.21 | 13 | Clontech | tetramer |
| mRFP1 | 584 | 607 | ~30k | 0.25 | | Tsien lab | monomer |
| J-Red | 584 | 610 | | 0.20 | 8.8 | 13 | | dimer |
| mCherry | 587 | 610 | | 0.22 | 16 | 96 | Clontech | monomer |
| HcRed1 | 588 | 618 | ~52k | 0.03 | 0.6 | Clontech | dimer |

Figure 1 - F

| | | | | | | | | |
|---|---|---|---|---|---|---|---|---|
| mKate2 | 588 | | 26k | 0.40 | 25 | + | Evrogen | monomer |
| Katushka (TurboFP365) | 588 | | 26k | 0.34 | 22 | ++ | Evrogen | dimer |
| mKate (TagFP635) | 588 | | | 0.30 | 15 | | Evrogen | monomer |
| TurboFP365 | 588 | | 26 k | 0.34 | 22 | | Evrogen | dimer |
| mPlum | 590 | | | 0.10 | 4.1 | 53 | Clontech | |
| mRaspberry | 598 | | | 0.15 | 13 | | Clontech | monomer; faster photobleach than mPlum |
| mNeptune | 600 | | | 0.20 | 13 | | Tsien Lab | monomer |
| E2-Crimson | 611 | | | 0.23 | 29 | | Clontech | |
| Other probes | | | | | | | | |
| Monochlorobimane | 380 | | 226 | Glutathione probe | | | | |
| Calcein | 496 | | 623 | pH > 5 | | | | |
| HyPer | 420/500 | | | Hydrogen peroxide sensor | | | | |

| Probe | Ex (nm) | Em (nm) | MW | Notes |
|---|---|---|---|---|
| Reactive and conjugated probes | | | | |
| Hydroxycoumarin | 325 | 386 | 331 | Succinimidyl ester |
| Aminocoumarin | 350 | 445 | 330 | Succinimidyl ester |
| Methoxycoumarin | 360 | 410 | 317 | Succinimidyl ester |
| Cascade Blue | 375;400 | 423 | 596 | Hydrazide |
| Lucifer yellow | 425 | 528 | | |
| NBD | 466 | 539 | 294 | NBD-X |
| R-Phycoerythrin | 480;565 | 578 | 240,000 | |
| PE-Cy5 conjugates | 480;565;650 | | | aka Cychrome, Tri-Color, Quantum Red |
| Red 613 | 480,565 | 613 | | PE-Texas Red |
| Red 670 | 480,565 | | | |
| Fluorescein | 495 | 519 | 389 | FITC; pH sensitive |
| BODIPY-FL | 503 | 512 | | |
| Cy3 | 512,552 | 565,615 | | |

Figure 1 - G

| | | | | |
|---|---|---|---|---|
| TRITC | 547 | 572 | 444 | TRITC |
| X-Rhodamine | 570 | 576 | 548 | XRITC |
| Lissamine Rhodamine B | 570 | 590 | | |
| Texas Red | 589 | 615 | 625 | Sulfonyl chloride |
| Cy5 | 625-650 | | | |
| Allophycocyanin | | | 104,000 | |
| Nucleic acid probes | | | | |
| Hoechst 33342 | 343 | 483 | | |
| DAPI | 345 | 455 | | |
| Hoechst 33258 | 345 | 478 | | |
| Chromomycin A3 | 445 | 575 | | |
| Mithramycin | 445 | 575 | | |
| Thiazole Orange | 453 | 480 | | |
| YOYO-1 | 491 | 509 | | |
| Ethidium Bromide | 493 | 620 | | |
| Acridine Orange | 503 | 530/640 | | DNA/RNA |
| TOTO-1, TO-PRO-1 | 509 | 533 | | Vital stain |
| Propidium Iodide (PI) | 536 | 617 | 668 | |
| TOTO-3, TO-PRO-3 | | | | |
| Cell function probes | | | | |
| Indo-1 | 361/330 | 490/405 | 1010 | AM ester. Low/High Ca2+ |
| Fluo-3 | 506 | 526 | 855 | AM ester. pH > 6 |
| 2'7'Dichorodihydrofluorescein (DCFH) | 505 | 535 | 529 | Oxidized form |
| Dihydrorhodamine 123 (DHR) | 505 | 534 | 346 | Oxidized form. Light catalyzes oxidation |
| SNARF | 548/579 | 587/635 | | pH 6/9 |
| Green Fluorescent Proteins | | | | |
| Y66F | 360 | 508 | | |
| Y66H | 360 | 442 | | |
| Y66W | 436 | 485 | | |
| Wild Type | 396,475 | 508,503 | | |
| S65A | 471 | 504 | | |
| S65C | 479 | 507 | | |
| S65L | 484 | 510 | | |
| S65T | 488 | 511 | | |
| Other probes | | | | |
| Monochlorobimane | 380 | 461 | 226 | Glutathione probe |
| Calcein | 496 | 517 | 623 | pH > 5 |

Figure 1 - H

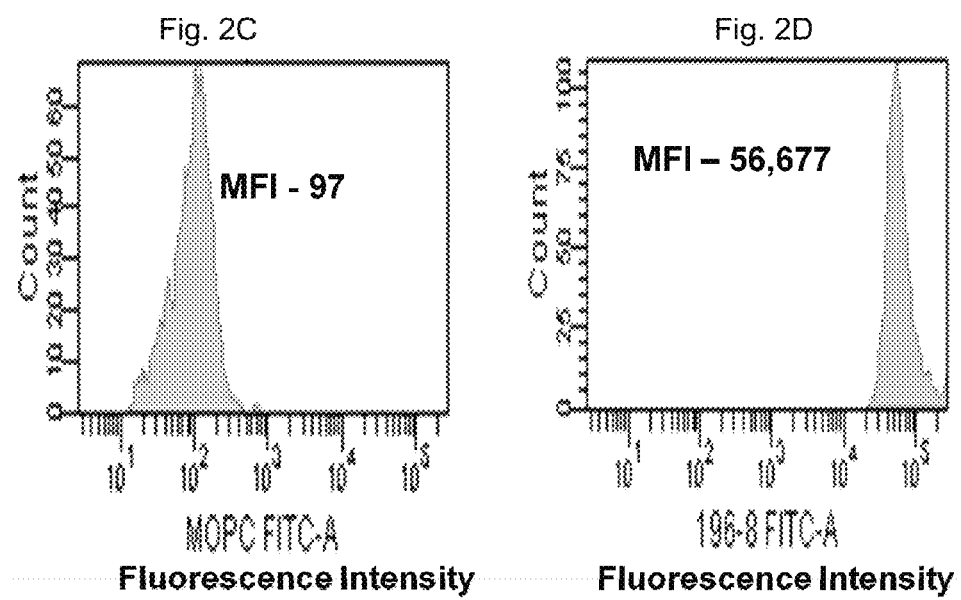

| IgG | ELISA | | | | IgA | ELISA | | | |
|---|---|---|---|---|---|---|---|---|---|
| | | + | - | Totals | | | + | - | Totals |
| FPA | + | 131 | 5 | 136 | FPA | + | 67 | 16 | 83 |
| | - | 8 | 106 | 114 | | - | 19 | 148 | 167 |
| | Totals | 139 | 111 | | | Totals | 86 | 164 | |

Sensitivity = 94%  Specificity = 96%   Sensitivity = 78% Specificity = 90%

| IgM | ELISA | | | | SRA | | | | |
|---|---|---|---|---|---|---|---|---|---|
| | | + | - | Totals | | | + | - | Totals |
| FPA | + | 54 | 6 | 60 | FPA | + | 134 | 2 | 136 |
| | - | 48 | 142 | 190 | | - | 16 | 98 | 114 |
| | Totals | 102 | 148 | | | Totals | 150 | 100 | |

Sensitivity = 53%  Specificity = 96%   Sensitivity = 89% Specificity = 98%

Figure 5A

HIT antibody results with sera from 100 normal subjects.

| Test | Negative | Positive | Reactive |
|---|---|---|---|
| SRA | 100 | 0 | 0 |
| PF4 ELISA – IgG | 100 | 0 | 0 |
| Flow Bead – IgG | 98 | 2 | 0 |
| PF4 ELISA – IgA | 100 | 0 | 0 |
| Flow Bead – IgA | 99 | 1 | 0 |
| PF4 ELISA – IgM | 81 | 4 | 15 |
| Flow Bead – IgM | 96 | 4 | 0 |

Figure 5B

METHOD OF SIMULTANEOUS DETECTION OF HEPARIN-INDUCED IMMUNOGLOBULINS TYPES G, A, AND M

CROSS-REFERENCE TO RELATED APPLICATIONS

This application claims priority to U.S. Ser. No. 61/776,959, filed Mar. 12, 2013 and incorporated by reference herein.

STATEMENT REGARDING FEDERALLY SPONSORED RESEARCH

Not applicable.

BACKGROUND

Heparin is a highly sulfated glycosaminoglycan (GAG) consisting of repeating disaccharide units with an average molecular weight of 12-15 kilodaltons (kD). Most heparin prepared commercially for infusion into human patients is isolated from the gut mucosa of pigs in the form termed "unfractionated heparin" (UFH). Fractionation of UFH by various methods results in low molecular weight heparin (LMWH) with 60% of the polysaccharide chains having a molecular weight less than 8 kD.

The anticoagulant effect of UFH is mediated by interactions with anti-thrombin (AT), a serine protease inhibitor of thrombin. Binding of UFH to AT activates and accelerates inhibition by AT of the coagulation proteases thrombin and Factor Xa. It is estimated that about one third of hospitalized patients or 12 million patients per year receive UFH and LMWHs for a wide range of surgical and therapeutic procedures. However, about 1-5% of patients injected with heparin develop the disorder "heparin-induced thrombocytopenia" (HIT).

HIT is an adverse reaction to heparin, in which affected patients produce platelet-activating antibodies that bind complexes of platelet-factor 4 (PF4) and heparin (HIT antibodies), resulting in a prothrombotic and thrombocytopenic condition that in severe cases can be life-threatening. As many as 600,000 people per year develop HIT, which is double the number of breast cancer cases diagnosed annually in the United States (US Cancer Statistics Working Group), and nearly equal to the number of new cases of angina diagnosed each year (Go 2013). Failure to diagnose HIT can lead to catastrophic thrombosis if heparin therapy is continued. It is therefore important that a quick and accurate diagnosis of HIT is made when it occurs. An accurate diagnosis of HIT requires attention to both clinical findings and laboratory test results.

Conventional treatment for patients suspected of having HIT includes the immediate cessation of all heparin followed by prompt administration of a non-heparin parenteral anticoagulant (Cuker 2012). Thus, a rapid and reliable serologic test capable of detecting HIT antibodies and fully characterizing their potency and molecular properties can be extremely helpful to a clinician who is called upon to make these management decisions. One widely used immunologic assay is the PF4/heparin ELISA (PF4 ELISA), in which PF4 in a complex with UFH or another high molecular weight polyanion is bound to the wells of a plastic microtiter plate to serve as antigen. After incubation with highly diluted patient's serum, which potentially contains the antibodies of interest, and washing of the well, the presence of bound antibodies is detected with an enzyme-labeled anti-human immunoglobulin reagent.

The PF4 ELISA has a sensitivity for antibody detection approaching 100%, but a low positive predictive value for HIT diagnosis. Further, the ELISA is time consuming, costly and thus is normally not performed for single determinations but used to assay multiple samples, thus delaying the diagnosis process.

A recognized shortcoming of PF4 ELISA testing is that some patient serum samples that do not contain clinically significant HIT antibodies produce positive reactions in the PF4 ELISA (Whitlach 2010). To distinguish these false-positive reactions from true positives, it is a common practice to test patient samples in two wells, adding high dose heparin (typically 100 U/mL) to the second well. A true positive reaction will be inhibited by high dose heparin but a false positive will not, enabling the distinction between the two types of reactions to be made. The need for a high dose heparin step doubles the cost of PF4 ELISA testing.

An alternative method to confirm the presence of HIT antibodies is to use a functional assay such as the $^{14}C$-serotonin release assay (SRA), in which a positive test result correlates better with the clinical picture of HIT. The SRA involves incubation of patient's serum and various doses of UFH with washed platelets loaded with radioactive $^{14}C$-labeled serotonin. Sera from m patients with HIT having IgG antibodies form immune complexes with PF4/heparin, and the Fc portion of IgG incorporated into these complexes engages FcγRIIa (CD32) receptors on the labeled platelets, causing platelet activation and release of $^{14}C$-serotonin that can be measured in a beta counter instrument. The SRA is a technically demanding and expensive test performed routinely in only a few specialty laboratories. It is therefore impractical to perform the SRA on a timely basis when HIT is suspected and antibody detection is urgently needed to aid in patient management decisions. In addition, the high cost of the SRA, its limited availability, and the requirement for use of radioactivity make it less practical from a laboratory perspective than other approaches, particularly the invention described herein.

Most HIT antibodies are of the IgG isotype. However, IgA antibodies are common and IgM antibodies are not rare (Suh 1997, Greinacher 2007). It has been claimed by some that only IgG antibodies cause clinically significant HIT and that IgA and IgM antibodies need not be detected (Linhoff-Last 2001, Warkentin 2003). However, others have reported that HIT antibodies of the IgM and IgA isotypes can cause severe disease (Amiral 2006, Davoren 2006). Until this controversy is settled, it is important that test platforms be available that can distinguish between the three Ig isotypes. To achieve this using the standard PF4 ELISA format requires that three wells be utilized for each test, one each for secondary antibodies specific for IgG, IgA and IgM. If the high dose heparin inhibition step is added, a total of six wells would be needed for each test, greatly increasing the cost and turn-around time of each patient result. In part for this reason, testing for all three HIT antibody isotypes is not widely available currently.

Despite the high sensitivity of the PF4 ELISA and high specificity of the SRA, the shortcomings of these testing methods described above indicate a need for an assay capable of detecting HIT antibodies of the IgG, IgA and IgM isotypes, preferably rapidly and at low cost and preferably in a single reaction mixture.

BRIEF SUMMARY OF THE INVENTION

The inventors provide an assay for rapid detection of HIT antibodies of various isotypes such as IgG, IgA, and IgM in a single tube on a solid support, preferably a particle such as a bead. The use of secondary antibodies with different labels, preferably fluorophores, to simultaneously detect HIT antibodies of multiple isotypes offers several operational advantages, including labor and material efficiencies and conservation of clinical sample volumes. In addition, this assay preferably avoids false-positive reactions of the type seen in the standard PF4 ELISA, thereby avoiding the need for a confirmatory step using high dose heparin and enables more rapid turnaround than conventional PF4 ELISA testing.

In one embodiment, the invention provides a method of detecting HIT antibodies in a patient sample, preferably a serum sample, comprising a) obtaining a sample from a patient suspected of having HIT; b) contacting the sample to bound PF4/heparin complexes displayed on a solid surface, wherein HIT antibodies within the patient sample bind to the complexes; c) contacting the HIT antibodies bound to the PF4/heparin complexes bound to the solid surface of step (b) with at least two secondary antibodies labeled with different labels, wherein the secondary antibodies bind to the HIT antibodies bound to the complexes and wherein the antibodies are labeled so that the different labels indicate binding to different antibody isotypes; d) detecting the presence of the labels used and e) determining the presence of HIT antibodies by measuring the strength of the signals emitted by the labels. In one embodiment, the at least two secondary antibodies are anti-human immunoglobulins selected from the group consisting of anti-Ig, anti-IgG, anti-IgA, and anti-IgM.

The invention also provides a kit for determining the presence or absence and relative strength of HIT antibodies in a sample. The kit comprises (a) a particulate solid support prepared by adding PF4 to a solid surface to which heparin has been attached, (b) at least two labeled anti-human immunoglobulin antibodies with labels that can be distinguished from each other; and (c) instructions for use. In one embodiment, the at least two secondary antibodies are anti-human antibodies selected from the group consisting of anti Ig, anti-IgG, anti-IgA, and anti-IgM.

One of skill in the art would know that various similarly acting materials or conditions can be substituted for those described here. These substitutions could be for the solid surface, the antigen, the method of attaching the antigen to the solid surface, the range of dilutions used for the antibodies, the buffers used in the reactions with the beads, the source of the patient antibodies, the incubation times, the species of the secondary antibodies, the labels used with the secondary antibodies, and the detection format for the labeled antibodies.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

BRIEF DESCRIPTION OF THE DRAWINGS

The patent or application file contains at least one drawing in color. Copies of this patent or patent application publication with color drawings will be provided by the Office upon request and payment of the necessary fee.

FIG. 1A-H. Characteristics of fluorophores useful for flow cytometry or fluorescence microscopy. Within groups, roughly in order of excitation wavelength (families excepted). Peak excitation and emission wavelengths often vary depending on the environment in which the probe finds itself.

FIG. 2C-D is another flow cytometry histogram showing similar data but in a more clear form with both peaks represented and the mean fluorescent data included on each histogram. Again PF4-heparin complexes displayed on the beads were incubated with negative control monoclonal antibody FIG. 2C, and anti-PF4 specific monoclonal antibody FIG. 2D and bound monoclonal antibody was again detected with FITC-anti-mouse IgG. Note the shift from a mean fluorescent intensity of 97 to 56,677, an increase in fluorescent intensity of 584 fold.

FIG. 5A. Comparison of results obtained with the FBA to those obtained with the PF4 ELISA and SRA assays. A total of 250 serum samples from patients previously tested by SRA were used. Sixty percent were SRA-positive and 40 percent were SRA-negative. FIG. 5B. HIT antibody results obtained with serum from 100 normal blood donors using SRA, PF4 ELISA, and FBA. Note that 15 of the normal samples gave a "positive" test result in the PF4 ELISA that was not inhibited when high dose heparin was used, i.e., produced a "reactive" (false positive) readout. All these samples were negative in the FBA.

DETAILED DESCRIPTION OF THE INVENTION

Figure 2A:
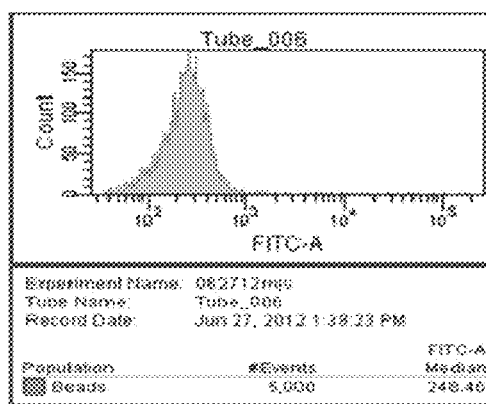
FIG. 2A-B. Flow cytometry fluorescence histograms show platelet factor 4 (PF4)-heparin complexes successfully bound to end-linked heparin covalently linked to beads. PF4-heparin complexes displayed on the beads were incubated with negative control monoclonal antibody (FIG. 2A), and anti-PF4 specific monoclonal antibody (FIG. 2B) and bound monoclonal antibody was detected with FITC-anti-mouse IgG. It was evident that a significant amount of PF4 (bound to end-linked heparin displayed on the beads) was detected on the beads, as evidenced by the pronounced shift to the right in the fluorescence histogram (FIG. 2B) and high median fluorescence intensity (262,000) more than 1000× higher than that obtained with beads incubated with negative control monoclonal (248) (FIG. 2A).

In the most preferred embodiment, the invention provides a method of detecting HIT antibodies in a patient comprising a) obtaining a sample from a patient suspected of having HIT; b) allowing the PF4 to bind to heparin fragments bound securely to a solid surface to form PF4/heparin complexes; c) contacting the sample to the bound PF4/heparin complexes, wherein the HIT antibodies bind to the complexes; d) contacting the HIT antibodies that bind to this target with at least two fluorophore-labeled secondary antibodies, wherein the secondary antibodies bind to the HIT antibodies bound to the complexes; e) detecting the fluorophore labels that bind to the HIT antibodies and f) determining the presence of HIT antibodies by measuring the strength of the signals emitted by one or more of the fluorophores. In one embodiment, the at least two secondary antibodies are anti-human immunoglobulins selected from the group consisting of anti-Ig, anti-IgG, anti-IgA, and anti-IgM.

In a preferred embodiment, the invention provides a method of detecting HIT antibodies comprising a) obtaining a sample from a patient suspected of having HIT; b) allowing the PF4 to bind to heparin fragments end-linked to a polystyrene bead to form PF4/heparin complexes; c) contacting the sample to the bound PF4/heparin complexes, wherein the HIT antibodies bind to the complexes; d) contacting the HIT antibodies that bind to this target with at least two fluorophore-labeled secondary antibodies, wherein the secondary antibodies bind to the HIT antibodies bound to the complexes; e) detecting the fluorophore labels that bind to the HIT antibodies and f) determining the presence of HIT antibodies by measuring the strength of the signals emitted by one or more of the fluorophores. In a preferred embodiment, one would use end-linked heparin to combine or complex with PF4 as the antigen. In a preferred embodiment, one would use purified PF4 or recombinantly produced PF4. One could also use crude platelet lysates, containing large amounts of PF4. In one embodiment, the at least two secondary antibodies are anti-human immunoglobulins selected from the group consisting of anti-Ig, anti-IgG, anti-IgA, and anti-IgM.

In one embodiment, the invention provides a method of detecting HIT antibodies comprising a) obtaining a sample from a patient suspected of having HIT; b) allowing the PF4 to bind to heparin fragments end-linked to a polystyrene plate to form complexes; c) contacting the sample to the bound PF4/heparin complexes, wherein the HIT antibodies bind to the complexes; d) contacting the HIT antibodies that bind to this target with at least two fluorophore-labeled secondary antibodies, wherein the secondary antibodies bind to the HIT antibodies bound to the complexes; e) detecting the fluorophore labels that bind to the HIT antibodies and f) determining the presence of HIT antibodies by measuring the strength of the signals emitted by one or more of the fluorophores. In one embodiment, the at least two secondary antibodies are anti-human immunoglobulins selected from the group consisting of anti-Ig, anti-IgG, anti-IgA, and anti-IgM.

The invention also provides a kit for measuring the level of HIT antibodies or their presence in a sample. The kit comprises (a) a solid support prepared by adding PF4 to a solid surface to which heparin has been attached (b) at least two labeled anti-human immunoglobulin antibodies with unique labels; and (c) instructions for use. In one embodiment, the at least two secondary antibodies are anti-human antibodies selected from the group consisting of Ig, IgG, IgA, and IgM and the labels are fluorophores.

In one embodiment, the antigen is bound to a solid surface using a covalent chemical reaction to bind the heparin molecules to the bead surface, such as, for example, by the reductive amination (Hoffman 1983, Suh 1998) to amino groups on amino-modified microsphere beads. However, one could also use antibodies or linker proteins to bind PF4 to the surface of the bead and then bind heparin or another GAG to that to form a suitable PF4-heparin target for antibody detection.

A preferred embodiment of the invention provides an improved multiplex flow cytometry bead assay (FBA) that utilizes polystyrene beads coated with PF4/heparin complexes for simultaneously detecting IgG, IgA, and IgM antibodies specific to HIT. Other isotypes of antibodies such as those for sIgA, IgD or IgE could also be included as secondary antibodies in the invention. One could also include secondary antibodies to ascertain the subtypes of immunoglobulin such as IgG1 or IgG2 for example. The method of the present invention has the advantages of simultaneously detecting Ig, IgG, IgA, and IgM antibodies individually and specifically more rapidly and with improved specificity and sensitivity than conventional testing methods, all in the same reaction mixture.

I. In General

In the specification and in the claims, the terms "including" and "comprising" are open-ended terms and should be interpreted to mean "including, but not limited to . . . ." These terms encompass the more restrictive terms "consisting essentially of" and "consisting of."

As used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

Other elements of the assay can be modified to suit the needs of the skilled practitioner. For instance, the dilutions, buffers, incubation times and labels used may all vary depending on the needs of the practitioner.

Dilutions. In one embodiment, dilution for patient sample is 1:50. However other dilutions in the range of 1:10 to 1:500 may be satisfactory, depending on the needs of the user as determined by one of skill in the art. The most preferred dilution of patient sample used herein is a 1:50 dilution of serum however other dilutions in the range of 1:2 to 1:10,000, depending on the strength of the antibody response in the patient, would work. The most preferred sample type would be serum however, we predict that whole blood or plasma would be satisfactory. For instance, dilutions in the range of 1:10 to 1:2 can be suitable but may not be practical from the standpoint of conservation of clinical sample. Dilutions above 1:500 may be suitable for samples containing potent antibodies.

Buffers. In a preferred embodiment, PBS would be used for antibody antigen reactions. However, most isotonic and physiologic solutions known to the art would be satisfactory.

Incubation times. In a preferred embodiment, one would allow the antigen antibody reactions to occur over 5 to 60 minutes and most optimally 30 minutes. However, longer incubations could be preformed for convenience as identified by one of skill in the art.

Fluorophores. In one embodiment, each secondary antibody used in the method of this invention is fluorophore-labeled using a unique fluorophore. For instance, in one embodiment, one of skill in the art would use three antibodies specific to human IgG, IgA and IgM respectively, labeled with fluorophores having emission spectra as non-overlapping as possible, such as, for example, FITC, APC and PE. Substitutions of fluorophore labeled secondary antibodies could be used so that one could distinguish the fluorescent emission of the fluorophore by use of detection lasers present in the flow cytometry equipment. There is no limit to how close the emission spectra of the fluorophores must be. However, it is generally accepted to look for fluorophores that use different lasers for detection. Some degree of overlap in emission spectra is acceptable but it is generally accepted to use emission spectra as far apart as possible.

Flow Cytometry. Flow cytometry is a laser based, biophysical technology employed in cell counting, sorting, biomarker detection and protein engineering, by suspending cells in a stream of fluid and passing them by an electronic detection apparatus. It allows simultaneous analysis of the physical and/or chemical characteristics of up to thousands of particles per second. Flow cytometry is routinely used in the diagnosis of health disorders, for example blood cancers, but has many other applications in basic research, clinical practice and clinical trials. A common variation is to physically sort particles based on their properties, so as to purify populations of interest.

In one embodiment of the invention, flow cytometry with lasers capable of detecting the fluorophore-labeled secondary antibodies is used to detect the presence of the HIT antibodies. The flow cytometry assay for detection of HIT antibodies is easily and rapidly carried out in any clinical laboratory under standard conditions using standard reagents and technology. In a patient suspected of having HIT, it can be determined immediately diagnosed whether HIT antibodies are present or absent with the method of the present invention. However, other methods of detecting the fluorophore labeled secondary antibodies known to the art may also be used. For instance, a Luminex type of platform would detect fluorophore labeled beads or an ELISA plate reader capable of reading fluorescence could also be used.

II. Definitions

By "antigen" we mean a target complex consisting of human PF4 complexed with a glycosaminoglycan, such as heparin.

By "diagnosing" we mean classifying a pathology (e.g., a cancer or a pre-malignant lesion) or a symptom, determining a severity of the pathology (grade or stage), monitoring pathology progression, and forecasting an outcome of a pathology and/or prospects of recovery.

By "bound securely to a solid surface" we mean any method which would bind an element to a second element in a way that said elements would not become disassociated including but not limited to covalent linkage, chemical end-linking, use of avidin and biotin on each of the elements, or use of a high affinity antibody to the first element and a second element bound securely to a surface by one of the aforementioned methods.

By "fluorophore" we mean a chemical compound which, upon being exposed to light of one wavelength, re-emits light of a different wavelength, which can be detected to provide a measure of the quantity of chemical present. A preferred flourophore is one that emits light in the visible spectrum.

By "HIT" we mean heparin-induced thrombocytopenia, an adverse reaction to heparin, in which affected patients produce platelet-activating antibodies that bind complexes of platelet-factor 4 (PF4) and heparin, resulting in a prothrombotic and thrombocytopenic condition that in severe cases can be life-threatening.

By "HIT antibody" or "HIT antibodies" we mean antibody produced in a patient that causes or contributes to HIT. The antibodies of particular interest in the diagnostic assay are those that bind to PF4 when it is in a complex with heparin or another negatively charged, linear, high molecular weight molecule.

By "heparin-induced" we mean antibodies that result from exposure to heparin and are capable of causing HIT.

By "heparin" we mean any of a family of polysaccharide species whose chains are made up of alternating 1-4-linked and variously sulfated residues of a uronic acid and D-glucosamine. Heparin/PF4 complexes can be immobilized on a solid surface by several different methods known to the art. Heparin is a glycosoaminoglycan or GAG. Glycosaminoglycans have high degrees of heterogeneity with regards to molecular weight, disaccharide construction, and sulfation due to the fact that GAG synthesis, unlike proteins or nucleic acids, is not template driven, and dynamically modulated by processing enzymes. Based on core disacharides structure, GAGS are classified into four groups: Heparin/heparan sulfate (HSGAGs) and chondroitin/dermatan sulfate (CSGAGs) are synthesized in the golgi apparatus, where protein cores made in the rough endoplasmic reticulum are posttranslationally modified with O-linked glycosylations by glycosyltransferases forming a proteoglycan. Keratan sulfate may modify core proteins through N-linked glycosylation or O-linked glycosylation of the proteoglycan. The fourth class of GAG, hyaluronic acid, is not synthesized by the golgi, but rather by integral membrane synthases which immediately secrete the dynamically elongated disaccharide chain. Due to the similar nature of long negatively charged molecules like polyanions to heparin, we include other polyanions and specifically polyvinylsulfonate (PVS) in our definition of heparin since these are known in the art to be effective heparin substitutes. Due to the similar nature of GAGS, we predict that one could use various GAGS in place of heparin or unfractionated heparin and get similar results and thus also include GAGS in our definition of heparin since these are known in the art to be effective heparin substitutes.

By "instructions for use" we mean a publication, a recording, a diagram, or any other medium of expression which is used to communicate the usefulness of the invention for one of the purposes set forth herein. The instructional material of the kit can, for example, be affixed to a container which contains the present invention or be shipped together with a container which contains the invention.

By "label" we mean a chemical compound such as a fluorophore which, upon being exposed to light of one wavelength, re-emits light of a different wavelength, which can be detected to provide a measure of the quantity of chemical present. We also mean chemical compounds which can absorb or reflect light in the visible spectra. Additionally, we mean enzymatic labels which can convert a substrate into a product such as a colored product suitable for detection. By "patient" we mean any human suspected of having HIT. By "suspected of having HIT" we mean the patient exhibits clinical symptoms indicative of HIT, including, for example, a below normal platelet count, enlargement or extension of a previously diagnosed blood clot, or the development of a new blood clot elsewhere in the body. Additional symptoms indicative of HIT include fever, rash, chills, high blood pressure, shortness of breath and chest pain.

By "sample" we mean a specimen or culture obtained from a human or animal patient suspected of having HIT. Biological samples can be obtained from patients and encompass fluids, solids, tissues, and gases. In one embodiment, the source of the patient antibodies would be serum. However, plasma, whole blood, or other blood products such as platelet rich plasma and others will be satisfactory. Preferably, a sample of about 0.2 ml is needed for a test reaction. Such examples are not however to be construed as limiting the sample types applicable to the present invention.

By "secondary antibodies" we mean any secondary antibody specific to a human immunoglobulin and labeled, preferably with a fluorophore, to enable its detection. Appropriate fluorophore labels on secondary antibodies include for example, Allophycocyanin (APC)-conjugated AffiniPure F(ab')2 goat anti-human IgG, Fcγ specific, fluoroscein (FITC)-conjugated F(ab')2 goat anti-human IgA, α chain specific, and the like. Additionally, one could use a variety of species for the production of such secondary antibodies including but not limited to mouse, rat, goat, sheep, rabbit, donkey, horse, bovine, porcine, and monkey. These antibodies could be either polyclonal or monoclonal in nature. Secondary antibodies could be intact IgG or other Ig isotypes, F(ab')2 fragments, or Fab fragments.

By "solid surface" we mean any surface suitable for immobilization of the PF4-heparin complex (or other antigen). This immobilization could occur by covalent linkage of heparin fragments produced by controlled nitrous acid digestion of unfractionated heparin (Hoffman 1983, Suh 1998). The preferred solid support for this technique is polystyrene beads displaying a high concentration of amino groups on their surface suitable for chemical linkage using terminal formaldehyde groups present on heparin fragments produced by nitrous acid digestion (Hoffman 1983). Beads are particulate in nature. Other bead types include magnetic beads, microparticles and nanoparticles. Some nanoparticles have a metallic interior. Other solid supports could include ELISA plates of various configurations made of polystyrene or other plastics.

EXAMPLES

The following examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

Example 1

Materials

Serum Samples. One hundred serum samples from normal blood donors were obtained from those left over after infectious disease testing at BloodCenter of Wisconsin, and 250 patient sera were from patients suspected of having HIT that had previously been referred for testing to the Platelet & Neutrophil Immunology Lab, Blood Center of Wisconsin. All serum samples were de-identified to protect patient anonymity, and all studies were approved by the IRB of BloodCenter of Wisconsin.

Antibody reagents. Allophycocyanin (APC)-conjugated AffiniPure F(ab')2 goat anti-human IgG, Fcγ specific, fluoroscein (FITC)-conjugated F(ab')2 goat anti-human IgA, α chain specific, R-phycoerythrin (PE)-conjugated F(ab')2 Donkey anti-human IgM, Fc5μ specific, and goat F(ab')2 anti-mouse IgG-FITC were all purchased from Jackson ImmunoResearch Labs, West Grove, Pa. MOPC-21 mouse monoclonal IgG1 was purchased from Sigma Chemical, St. Louis, Mo. MBC196.8 mouse monoclonal anti-human PF4 was produced by and obtained from the Hybridoma Laboratory, Blood Research Institute, Blood Center of Wisconsin, Milwaukee, Wis.

Fragmentation of heparin. Controlled digestion of heparin with nitrous acid was performed as described (Suh 1998) to cleave the heparin into smaller fragments containing a free aldehyde for coupling to amino-modified beads. A solution of 9,000 IU/ml of UFH was prepared by mixing 4.5 ml of injectable UFH (Mekesson, San Francisco, Calif.) in 0.5 ml of deionized water, and the pH was adjusted to 2.5. A 0.22 M/L solution of sodium nitrite (Sigma Aldrich, St. Louis, Mo.) was added dropwise to the UFH over a period of two minutes as the mixture was incubated for 2 hours at room temperature (RT) with stirring. The pH was then adjusted to 7.0, and the fragmented heparin was dialyzed twice against 4 L of PBS using a Slide-A-Lyzer dialysis cassette (Pierce, Rockford, Ill.) having a molecular weight cutoff of 3.5 kD. The dialyzed solution, containing heparin fragments larger than 3.5 kD, was passed through a 0.2 μm filter (EMD Millipore Corporation, Billerica, Mass.) and stored at −80° C. until used.

Coupling of fragmented heparin and PF4 to polystyrene beads. Acid digestion of UFH produced heparin fragments of various molecular weights containing a formaldehyde group at the reducing terminus that can be linked by reductive amination (Hoffman 1983), to tertiary amine groups on amine-modified microspheres. A total of 6×10^7 amino-modified microspheres (Bangs Laboratories, Inc., Fishers, Ind.) were washed twice in 0.1 M/L NaHCO3 buffer, pH 5.0 (coupling buffer). A 15% solution of fragmented heparin in coupling buffer containing 47.7 mM NaBH3CN (Sigma Chemical) was incubated with the washed beads at RT for 4 hours. Previous studies comparing a range of fragmented heparin concentrations showed 15% was optimum (results not shown). Beads were then washed ×3 with PBS TWEEN® polysorbate nonionic surfactant buffer (0.02 M/L PBS with 0.05% TWEEN® 20 polysorbate nonionic surfactant. pH 7.4) and stored in PBS TWEEN® polysorbate nonionic surfactant with 0.05% sodium azide at 4° C. for up to 4 weeks.

PF4 was allowed to form a complex with heparin-coated beads by incubating 6×10$^7$ heparin-coated beads with 9 ml of 10 μg/ml PF4 purified from human platelets GTI-Immucor, Waukesha, Wis.) in a 15 ml tube for 1 hour at 4° C. with mixing. Beads were washed twice with PBS TWEEN® polysorbate nonionic surfactant (PBS-TW), and then suspended in PVX (1:4 mix of 1% polyvinylpyrrolidone with 1% polyvinyl alcohol). PF4-heparin beads were stored at 4° C. for up to 1 week.

Flow Cytometry PF4 Bead Assay. Serum diluted 1:50 in PBS or PBS containing 100 U/mL UFH and 1×10$^5$ heparin-PF4 beads were incubated in the wells of a polystyrene microtiter plate for 30 minutes at RT. Following incubation, beads were washed three times with 0.05% PBS-TW, and incubated for 20 minutes at room temperature (RT) in the dark with a mixture of goat anti-human IgG-APC, goat anti-human IgA-FITC, and donkey anti-human IgM-PE diluted in 0.05% PBS-TW buffer containing PVX blocking solution. Following incubation beads were washed once, suspended in 0.05% PBS-TW, and 5,000 bead events acquired by flow cytometry (FACSCanto II, Becton Dickinson, Mountainview, Calif.). Analysis of data was performed using FACSDiva software by applying forward scatter versus side scatter light gates of bead events, and displaying IgG (APC), IgA (FITC), and IgM (PE) fluorescence histograms and calculating median fluorescence intensity (MDFI) values for each sample. An MDFI FL ratio (FLR) cut-off value for a positive reaction was calculated by taking 4× the mean FLR of the normal control sera tested in each assay. Modifications of the same procedure were performed substituting monoclonal antibody, MBC196.8, specific for PF4, or isotype negative control monoclonal, MOPC-21, for human serum, and FITC-anti-mouse IgG for anti-human immunoglobulins, for detection of PF4-heparin complexes when preparing coated beads.

PF4/Heparin ELISA and SRA. Testing by PF4 ELISA and SRA was performed using in-house developed assays as previously described (McFarland 2012).

Figure 2B:
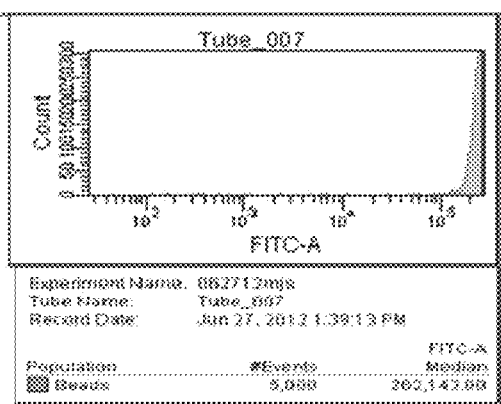
Figure 3:
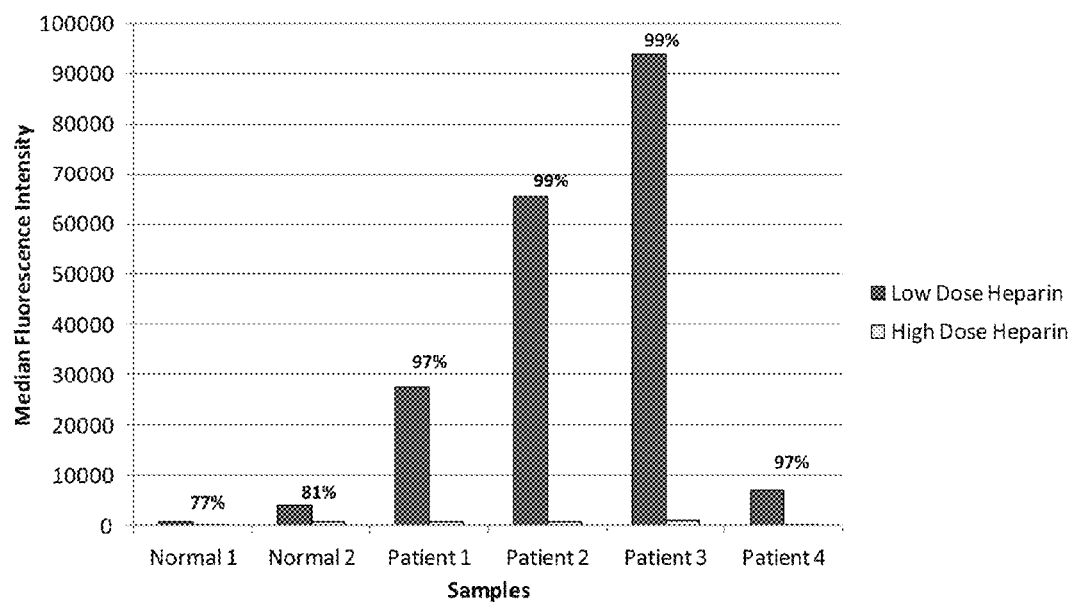
FIG. 3. Human sera containing or not containing HIT antibodies give expected results with PF4-heparin coated beads by flow cytometry for antibody detection. Serum samples were incubated with heparin/PF4 coated beads without added heparin or with 100 U/mL (High Dose Heparin) added heparin, washed with buffer ×3, incubated with APC-labeled anti-human IgG, and bead-bound fluorescence was measured using flow cytometry. Two sera from normal, healthy subjects tested negative as expected, and samples from 4 patients previously shown to have IgG HIT antibodies by both PF4 ELISA and SRA tested positive by the new flow cytometry bead assay. Specificity of positive results obtained with the 4 sera known to contain HIT antibodies was confirmed by demonstrating inhibition of fluorescence signal ≥50% (% values shown) in the presence of high dose heparin.

Quality Control of heparin-PF4 Beads. To determine whether heparin-PF4 complexes had formed on the surface of the microspheres during preparation, we tested the microspheres by flow cytometry with a monoclonal antibody specific for PF4 (MBC196.8). Fluorescence values (MDFI=262, 000) for beads incubated with anti-PF4 monoclonal were over 1000× higher than the same beads incubated with control monoclonal (MDFI=249), indicating successful coupling of heparin and PF4 to the microspheres (FIG. 2). Additional testing of the beads by flow cytometry with 2 human sera that tested negative, and 4 sera that tested positive previously by both PF4 ELISA and SRA gave expected results (FIG. 3).

Figure 4:
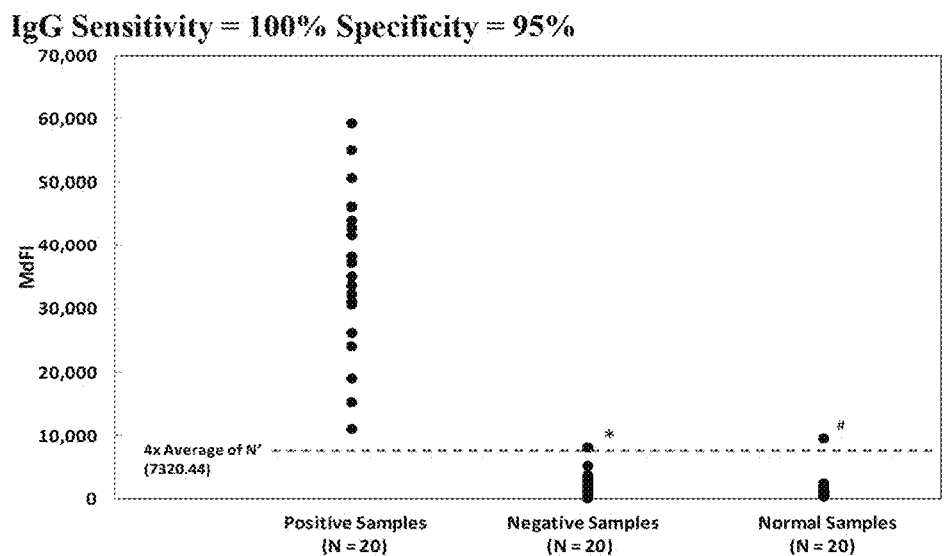
FIG. 4. Test results obtained using the new PF4 multiplex flow cytometry bead assay (FBA) for simultaneous detection of IgG, IgA, and IgM HIT antibodies. Serum samples that tested positive ("positive samples") or negative ("negative samples") in the PF4 ELISA and sera from normal blood donors ("normal samples") were tested by the new flow cytometry bead assay (FBA). Results shown are median fluorescence values (MdFI) from a single assay. Red dotted lines are cut-off values for a positive result calculated by taking 4× the mean obtained with the negative control sample for each assay. A) IgG antibody results for all samples matched those obtained previously by IgG PF4 ELISA with the exception of one negative patient sample marked on the figure with a (*) that gave a weak positive result, and one normal sample marked on the figure with a (#) that tested weakly positive in both the PF4 ELISA and the FBA but negative by SRA. B) IgA antibody results for all samples matched those obtained previously by IgA PF4 ELISA with the exception of weak positive results obtained by FBA with 3 negative samples. C) IgM antibody results matched IgM PF4 ELISA results for the negative and normal samples, but only 7 of 15 positive patient samples matched PF4 IgM ELISA results. This difference is explained by the higher rate of "false positive" test results for IgM antibodies by PF4 ELISA as shown in FIG. 5B, in which testing of 100 sera from normal, healthy blood donors with no known exposure to heparin by PF4 ELISA showed a total of 19 positive or "reactive" (failure to inhibit with high dose heparin) results compared to only 4 of 100 positive results by the new bead assay. We believe this difference is a result of the purposeful design of the FBA that uses PF4 complexed with end-linked heparin covalently linked to a spherical bead to provide a target for HIT antibodies similar to the in vivo presentation of PF4 bound to heparin-like molecules on the spherical surface of a human platelet.
Figure 4:
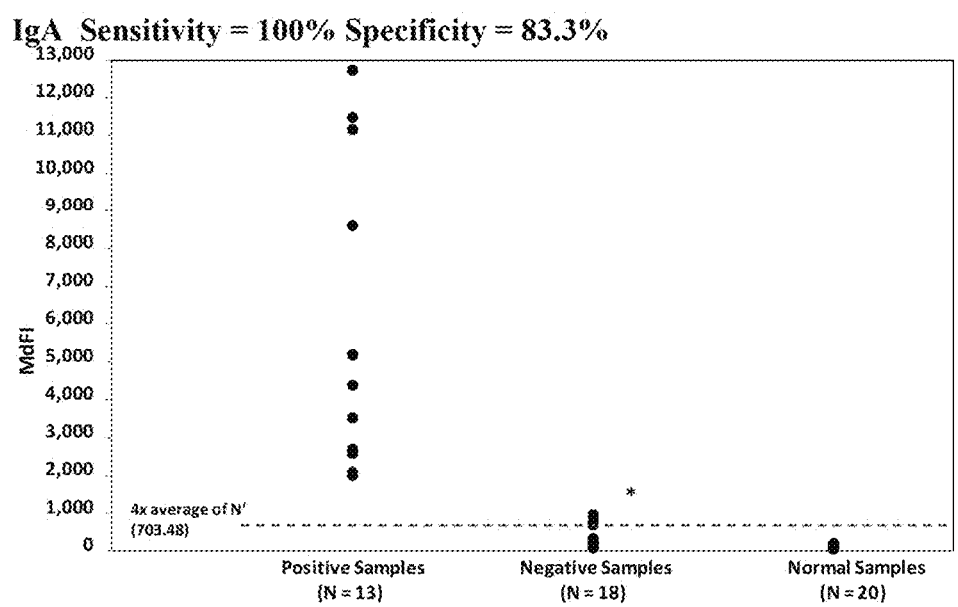
Figure 4C:
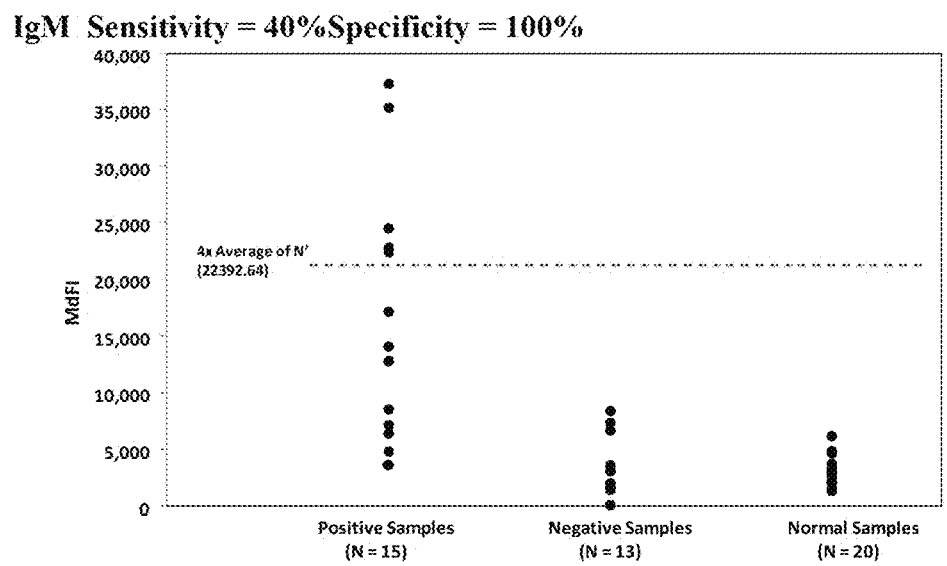

Simultaneous Detection of IgG, IgA, IgM PF4-Heparin Antibodies with PF4-Heparin Beads by Flow Cytometry. Twenty samples that previously tested positive and 20 that tested negative in the PF4 ELISA (results not shown), and 20 sera from normal blood donors were all tested by the new flow cytometry bead assay (FBA). IgG antibody results for all samples matched those obtained previously by IgG PF4 ELISA with the exception of one negative patient sample that gave a weak positive result, and one normal sample that tested weakly positive in both the PF4 ELISA and the FBA but negative by SRA (not shown), (FIG. 4). IgA antibody results for all samples matched those obtained previously by IgA PF4 ELISA with the exception of weak positive results obtained by FBA with 3 negative samples, and IgM antibody results matched IgM PF4 ELISA results for the negative and normal samples, but only 7 of 15 positive patient samples matched PF4 IgM ELISA results (FIG. 4).

Example 2

Detection of HIT Antibodies of the IgG, IgA and IgM Classes

Figure 6:
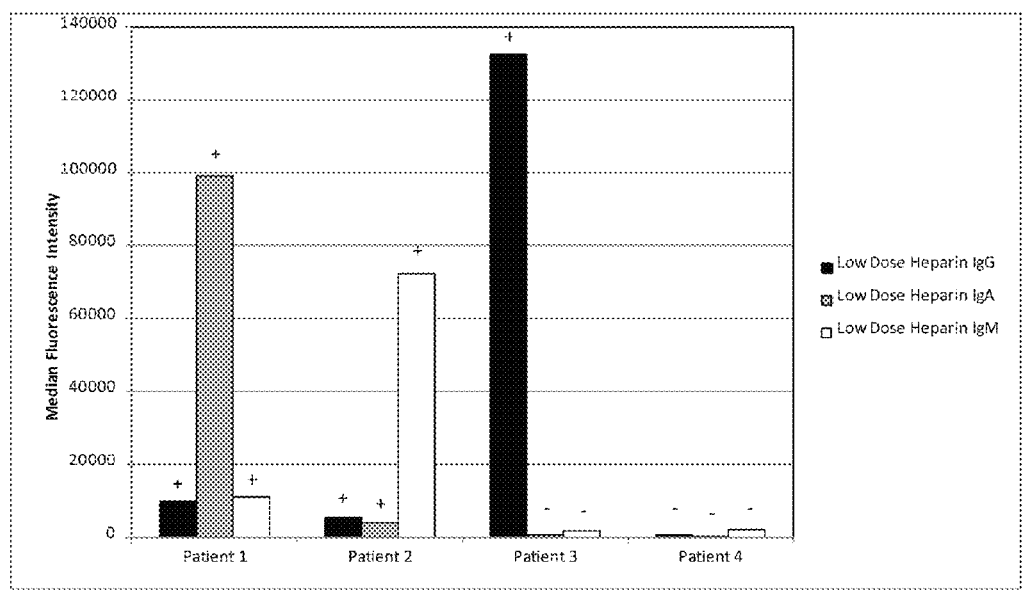
FIG. 6. Flow cytometry heparin/PF4 bead assay illustrating simultaneous detection of IgG, IgA, and IgM HIT antibodies in patient sera. Serum samples were incubated with heparin/PF4-coated beads, washed with buffer ×3, incubated with APC-labeled anti-human IgG, FITC-labeled anti-human IgA, and PE-labeled anti-human IgM, and bead-bound fluorescence was measured by flow cytometry. Results show the assay is capable of detecting the presence of IgG, IgA and IgM antibodies in patient 1 serum, which contains strong IgA (gray bar) antibodies and weaker IgG (black bar) and IgM (white bar) antibodies. Sample 2 was shown to contain strong IgM antibodies and weaker IgG and IgA antibodies, and sample 3 was shown to contain only strong IgG antibodies. Sample 4 was completely negative for antibodies.

As seen in FIG. 6, the method of the present invention can be used to simultaneously detect the presence of IgG, IgA, and IgM HIT antibodies in a patient sample. Detecting the presence of at least one HIT antibody, supports a diagnosis of HIT and failure to detect such an antibody argues strongly against the diagnosis. In use, one of skill in the art would identify a patient suspected of having HIT based on clinical observation or other data, obtain a sample from the patient, and test the sample for HIT antibodies of the IgG, IgA, and IgM classes or immunoglobulins of other types using the assay of the present invention.

This technique facilitates the accurate detection of HIT antibodies of the IgM classes, reducing the number of false positive results obtained by other methods. It has been suspected for some time that some positive IgM results obtained in the PF4 ELISA are due to non-specific binding of IgM immunoglobulins. Due to its polyvalent nature, IgM has very high avidity and binds tightly to its target but can also bind with lower avidity to off-target molecules or solid supports such as the polystyrene used in ELISA plates and beads. The method described herein provides a more accurate and specific identification of IgM antibodies that are specific to the heparin-PF4 complex and are therefore "HIT antibodies." Improved performance of the FBA may be due to the nature of the solid support used, the combination of secondary antibodies used for detection, or other assay conditions. The present invention enables detection of HIT antibodies of the IgG, IgA, and IgM isotypes separately in a single reaction mixture, enabling clinicians to consider only the IgG result or all three reactions depending on their preference.

Another potential advantage of a preferred embodiment of the present invention is the nature of the solid support when it is a bead. The three dimensional structure of the bead may mimic that of a cell in vivo (i.e., a platelet or endothelial cell with GAG attached), unlike the two dimensional presentation of the complex by a well of a microtiter plate as occurs in the popular ELISA format. Moreover, presentation of PF4 bound to end-linked heparin may mimic the target seen by an HIT antibody in vivo more closely than complexes of heparin and PF4 displayed on a microtiter plate surface as in the standard PF4 ELISA (Rauova 2006). Thus, this special presentation of the PF4/heparin complex may better preserve epitopes recognized by HIT antibodies and be less prone to non-specific recognition by non-HIT antibodies. Support for this is evident by the fact that the bead assay described herein does not require the use of high dose heparin (100 U/ml) to confirm that an antibody is, in fact, an HIT antibody. In the single antibody species ELISA format currently in use, a second high dose heparin condition is required to disrupt the target PF4/heparin complex, reducing HIT antibody binding by 50% or more. In addition, significantly fewer "false positive" IgM antibody results are obtained with the bead assay compared to the PF4 ELISA that uses PF4-PVS complexes bound to the flat well of a plastic microtiter plate (FIG. 5B).

Yet another potential advantage of the use of end-linked heparin bound to PF4 as the target for antibody detection is its improved specificity for HIT antibodies, obviating the need for a second high dose heparin step in antibody testing. We covalently attach the heparin to the bead through free aldehyde groups created on UFH by controlled digestion with nitrous acid, which is then linked to an $NH^2$ group on the bead.

Example 3

Comparison of the Invention with Conventional Assays

As shown in FIG. 5, the method of the present invention provides an improved method of detecting HIT antibodies as compared to conventional ELISA and SRA methods. Note that 15 of the normal samples gave a "positive" test result in the PF4 ELISA. That positive result was not inhibited when high dose heparin was used, i.e., produced a "reactive" (false positive) readout. All these samples were negative in the FBA while four positive samples were detected using both the PF4 ELISA and the FBA.

The above description, attached figures, and below claims are intended to be illustrative and not limiting of this invention. Many themes and variations of this invention will be suggested to one skilled in this and, in light of the disclosure. All such themes and variations are within the contemplation hereof. For instance, while this invention has been described in conjunction with the various exemplary embodiments outlined above and in the below claims, various alternatives, modifications, variations, improvements, and/or substantial equivalents, whether known or that rare or may be presently unforeseen, may become apparent to those having at least ordinary skill in the art. Various changes may be made without departing from the spirit and scope of the invention. Therefore, the invention is intended to embrace all known or later-developed alternatives, modifications, variations, improvements, and/or substantial equivalents of these exemplary embodiments.

REFERENCES

Albrecht Leo and Susanne Winteroll. Laboratory Diagnosis of Heparin-Induced Thrombocytopenia and Monitoring of Alternative Anticoagulants Clin. Diagn. Lab. Immunol. September 2003 10:5 731-740; doi:10.1128/CDLI.10.5.731-740.2003

Amiral J, Wolf M, Fischer A, Boyer-Neumann C, Vissac A, Meyer D. Pathogenicity of IgA and/or IgM antibodies to heparin-PF4 complexes in patients with heparin-induced thrombocytopenia. *Br J Haematol.* 1996; 92(4):954-959.

Arepally G M, Ortel T L. Heparin-induced thrombocytopenia. Annu Rev Med. 2010; 61:77-90

Cuker A, Cines D B: How I treat heparin-induced thrombocytopenia. Blood. 2012; 119: 2209-18.

Davoren A, Aster R H. Heparin-induced thrombocytopenia and thrombosis. *Am J Hematol.* 2006; 81(1):36-44.

Go A S, Mozaffarian D, Roger V L, Benjamin E J, Berry J D, Borden W B, Bravata D M, Dai S, Ford E S, Fox C S, Franco S, Fullerton H J, Gillespie C, Hailpern S M, Heit J A, Howard V J, Huffman M D, Kissela B M, Kittner S J, Lackland D T, Lichtman J H, Lisabeth L D, Magid D, Marcus G M, Marelli A, Matchar D B, McGuire D K, Mohler E R, Moy C S, Mussolino M E, Nichol G, Paynter N P, Schreiner P J, Sorlie P D, Stein J, Turan T N, Virani S S, Wong N D, Woo D, Turner M B: Heart disease and stroke statistics—2013 update: a report from the American Heart Association. Circulation. 2013; 127: e6-e245.

Gobbi G, Mirandola P, Tazzari P L, Ricci F, Caimi L, Cacchioli A, Papa S, Conte R, Vitale M Flow cytometry detection of serotonin content and release in resting and activated platelets. Br J Haematol. 2003 June; 121(6):892-6.

Greinacher A, Juhl D, Strobel U, et al. Heparin-induced thrombocytopenia: a prospective study on the incidence, platelet-activating capacity and clinical significance of antiplatelet factor 4/heparin antibodies of the IgG, IgM, and IgA classes. *J Thromb Haemost.* 2007; 5(8):1666-1673.

Hoffman J, Larme O, Scholander E: A new method for covalent coupling of heparin and other glycosaminoglycans to substances containing primary amino groups. Carbohydr Res 117:328, 1983

Lindhoff-Last E, Gerdsen F, Ackermann H, Bauersachs R. Determination of heparin-platelet factor 4-IgG antibodies improves diagnosis of heparin-induced thrombocytopenia. Br J Haematol 2001; 113: 886-890.

McFarland J, Lochowicz A, Aster R, Chappell B, Curtis B: Improving the specificity of the PF4 ELISA in diagnosing heparin-induced thrombocytopenia. Am J Hematol. 2012; 87: 776-81

Rauova L, Zhai L, Kowalska M A, Arepally G M, Cines D B, Poncz M. Role of platelet surface PF4 antigenic complexes in heparin-induced thrombocytopenia pathogenesis: diagnostic and therapeutic implications. Blood. 2006 Mar. 15; 107(6):2346-53.

Suh J S, Aster R H, and Visentin G P: Antibodies from patients with heparin-induced thrombocytopenia recognize multiple epitopes on heparin: PF4 complexes. Blood 91:916-922, 1998.

Suh J S, Malik M I, Aster R H, Visentin G P. Characterization of the humoral immune response in heparin-induced thrombocytopenia. *Am J Hematol.* 1997; 54(3):196-201.

Tazzari P L, Ricci F, Vitale M, Malferrari F, Salama A, Schwind P, Conte R. Heparin-induced thrombocytopenia: detection of antiheparin/PF4 antibodies by means of heparin/PF4-coated beads and flow cytometry. Transfus Med. 2002 June; 12(3):193-8.

Tomer A, Masalunga C, Abshire T C. Determination of heparin-induced thrombocytopenia: a rapid flow cytometric assay for direct demonstration of antibody-mediated platelet activation. Am J Hematol. 1999 May; 61(1):53-61.

US Cancer Statistics Working Group. United States Cancer Statistics: 1999-2009 Incidence and Mortality Web-based Report. Atlanta (Ga.): Department of Health and Human Services, Centers for Disease Control and Prevention, and National Cancer Institute; 2013. Available at: http://www.cdc.gov/uscs.

Warkentin T E. Heparin-induced thrombocytopenia: pathogenesis and management. Br J Haematol 2003; 121:535-555.

Warner M N, Pavord S, Moore J C, Warkentin T E, Hayward C P, Kelton J G. Serum-induced platelet procoagulant activity: an assay for the characterization of prothrombotic disorders. J Lab Clin Med. 1999 February; 133(2):129-33.

Whitlatch N L, Kong D F, Metjian A D, Arepally G M, Ortel T L. Validation of the high-dose heparin confirmatory step for the diagnosis of heparin-induced thrombocytopenia. Blood. 2010 Sep. 9; 116(10):1761-6

I claim:

1. A method of detecting heparin-induced thrombocytopenia (HIT) antibodies in a patient comprising:
   a) obtaining a serum or plasma sample from a patient suspected of having HIT;
   b) obtaining a solid surface to which a PF4/heparin complex has been bound;
   c) contacting the patient sample to the bound PF4/heparin complex, wherein HIT antibodies within the patient sample bind to the complex;
   d) contacting the bound HIT antibodies with at least a first and a second labeled secondary antibody, wherein the secondary antibody binds to the HIT antibodies bound to the complex and wherein the first antibody and the second antibody are specific for different isotypes selected from the group consisting of anti-Ig, anti-IgG, anti-IgA, and anti-IgM; and
   e) detecting the presence of HIT antibody isotypes based on the presence or absence of the label.

2. The method of claim 1 wherein the at least two secondary antibodies are anti-human antibodies selected from the group consisting of anti-Ig, anti-IgG, anti-IgA, and anti-IgM.

3. The method of claim 1 wherein the solid surface is a bead.

4. The method of claim 1 wherein the label is a fluorophore.

5. The method of claim 1 wherein the PF4/heparin complex is prepared using a covalent chemical reaction to bind the heparin molecules to the solid surface.

* * * * *